US008704029B2

(12) United States Patent
Nicholas et al.

(10) Patent No.: US 8,704,029 B2
(45) Date of Patent: *Apr. 22, 2014

(54) CONVERSION OF BUTYLENE TO PROPYLENE UNDER OLEFIN METATHESIS CONDITIONS

(75) Inventors: Christopher P. Nicholas, Evanston, IL (US); Etienne Mazoyer, Lyons (FR); Mostafa Taoufik, Villerbanne (FR); Jean-Marie Basset, Caluire (FR); Paul T. Barger, Arlington Heights, IL (US); James E. Rekoske, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 509 days.

This patent is subject to a terminal disclaimer.

(21) Appl. No.: 12/750,046

(22) Filed: Mar. 30, 2010

(65) Prior Publication Data
US 2011/0245570 A1    Oct. 6, 2011

(51) Int. Cl.
C07C 6/04    (2006.01)

(52) U.S. Cl.
USPC .......................... 585/646; 585/643

(58) Field of Classification Search
USPC .................................. 585/643, 646
See application file for complete search history.

(56) References Cited

U.S. PATENT DOCUMENTS

| | | | |
|---|---|---|---|
| 3,658,929 A * | 4/1972 | Banks | 585/324 |
| 3,691,095 A * | 9/1972 | Kroll et al. | 502/102 |
| 3,978,150 A | 8/1976 | McWilliams, Jr. | |
| 4,288,688 A | 9/1981 | Kiyama et al. | |
| 5,026,935 A | 6/1991 | Leyshon et al. | |
| 5,026,936 A | 6/1991 | Leyshon et al. | |
| 5,914,433 A | 6/1999 | Marker | |
| 6,166,279 A | 12/2000 | Schwab et al. | |
| 6,271,430 B2 * | 8/2001 | Schwab et al. | 585/644 |
| 6,646,172 B1 * | 11/2003 | Schwab et al. | 585/324 |
| 6,777,582 B2 * | 8/2004 | Gartside et al. | 585/324 |
| 6,858,133 B2 | 2/2005 | Dath et al. | |
| 7,087,155 B1 | 8/2006 | Dath et al. | |
| 7,214,841 B2 * | 5/2007 | Gartside et al. | 585/324 |

(Continued)

FOREIGN PATENT DOCUMENTS

| | | |
|---|---|---|
| CN | 1277608 C | 10/2006 |
| CN | 101172925 A | 5/2008 |

(Continued)

OTHER PUBLICATIONS

Taoufik, et al., "Direct Transformation of Ethylene into Propylene Catalyzed by as Tungsten Hydride Supported on Alumina: Trifunctional Single-Site Catalysis" in Angew. Chem. Int. Ed., 2007, 46, 7202-7205—2007, month unknown.*

(Continued)

Primary Examiner — In Suk Bullock
Assistant Examiner — Bradley Etherton
(74) Attorney, Agent, or Firm — Mark Goldberg

(57) ABSTRACT

Processes for the conversion, under conditions and with a catalyst system effective for olefin metathesis, of hydrocarbon feedstocks comprising butylene, for example all or a large proportion of a single $C_4$ olefin isomer such as butene-1, are described. Olefin products, and particularly propylene, are formed in the presence of a catalyst comprising a solid support and a tungsten hydride bonded to alumina present in the support. This occurs despite the expectation that the olefin metathesis reaction mechanism leads to the formation of olefin products having other carbon numbers.

20 Claims, 8 Drawing Sheets

(56) References Cited

U.S. PATENT DOCUMENTS

| | | | |
|---|---|---|---|
| 7,220,886 | B2 | 5/2007 | Podrebarac et al. |
| 7,268,265 | B1 | 9/2007 | Stewart et al. |
| 7,375,257 | B2 | 5/2008 | Dath et al. |
| 2006/0183627 | A1 | 8/2006 | Stephan et al. |
| 2007/0129584 | A1 | 6/2007 | Basset et al. |
| 2008/0194903 | A1 | 8/2008 | Schubert et al. |
| 2008/0255328 | A1* | 10/2008 | Basset et al. .......... 526/154 |

FOREIGN PATENT DOCUMENTS

| | | |
|---|---|---|
| EP | 936206 A1 | 10/2002 |
| EP | 1024123 B1 | 4/2004 |
| EP | 1831135 A2 | 9/2007 |
| EP | 2019814 A1 | 2/2009 |
| JP | 11217340 A | 8/1999 |
| WO | 2008071949 A1 | 6/2008 |
| WO | 2008153643 A1 | 12/2008 |

OTHER PUBLICATIONS

Leofanti, et al., "Surface Area and Pore Texture of Catalysts" in Catalysis Today, 41, 1998, 207-219—1998, month uknown.*

Delaude, et al., "Metathesis" in Kirk-Othmer Encyclopedia of Chemical Technology, John Wiley & Sons, 2001, published on-line Dec. 2, 2005.*

Merle, et al., "Selective and Unexpected Transformation of 2-Methylpropane to 2,3-dimethylbutane and 2-Methylpropene to 2,3-dimethylbutene Catalyzed by an alumina-Supported Tungsten Hydride" in Chem. Commun., 2009, 2523-2525—month unknown.*

Amigues et al., "Propylene from ethylene and 2-butene," Chinese Petroleum Corp., Hydrocarbon Processing. (ISSN 0018-8190) 69(10) Section1: 79-80 Gulf Publishing (Oct. 1990).

Huang et al., "Metathesis of ethene and 2-butene to propene on W/Al2O3-HY catalysts with different HY contents," Journal of Molecular Catalysis A; Chemical. 226(1): 61-68 Elsevier (2005).

Merle, "Selective and unexpected transformations of 2-methylpropane to 2,3-dimethylbutane and 2-methylpropene to 2,3-dimethylbutene catalyzed by an alumina-supported tungsten hydride", Chem. Commun., No. 18, Mar. 16, 2009, 2523-2525.

Le Roux, "Development of Tungsten-Based Heterogeneous Alkane Metathesis Catalysts Through a Structure-Activity Relationship", Angew. Chem., Int. Ed., 2005, 44, 6755-6758.

Search Report dated Feb. 20, 2014 for corresponding Japanese Appl. No. 2013-502693, Nicholas et al.

* cited by examiner

CONVERSION OF BUTYLENE TO PROPYLENE UNDER OLEFIN METATHESIS CONDITIONS

FIELD OF THE INVENTION

The invention relates to processes for the conversion of butylene to olefin products including propylene, under conditions and in the presence of a catalyst for olefin metathesis. A representative catalyst comprises a tungsten hydride bonded to alumina that is present in a support.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. Nos. 5,026,935 and 5,026,936. The cracking of olefins in hydrocarbon feedstocks, to produce these lighter olefins from $C_4$ mixtures obtained in refineries and steam cracking units, is described in U.S. Pat. Nos. 6,858,133; 7,087,155; and 7,375,257.

Steam cracking, whether or not combined with conventional metathesis and/or olefin cracking steps, does not yield sufficient propylene to satisfy worldwide demand. Other significant sources of propylene are therefore required. These sources include byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

The invention is associated with processes for the production of valuable light olefins such as propylene from butylene. More particularly, it has been surprisingly determined that butylene alone or present in a hydrocarbon feedstock comprising predominantly butylene (e.g., predominantly a single $C_4$ olefin isomer such as butene-1) can be converted to olefin products of lower and higher carbon numbers, with a high selectivity to propylene, using a particular olefin metathesis catalyst system. According to present understanding, the olefin metathesis reaction results in redistribution of alkylidene radicals that would be generated upon cleavage of the carbon-carbon double bond of an acyclic olefin. For example, in the case of self-metathesis, the reaction of a single olefin reactant with itself results in rearrangement of the olefinic carbon atom substituents according to the following reaction:

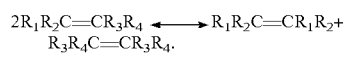

This reaction is described, for example, in US 2008/0255328, where $R_1$-$R_4$ represent hydrogen or hydrocarbon radicals, each of which is bonded to a carbon atom of the olefinic carbon-carbon double bond. Therefore, the self-metathesis of an asymmetrical olefin such as propylene ($R_1$, $R_2$, and $R_3$ are all —H and $R_4$ is —$CH_3$), produces both a lower carbon number olefin (e.g., ethylene) and a higher carbon number olefin (e.g., butene-2), as confirmed in working examples of US 2008/0255328, utilizing an alumina supported tungsten hydride catalyst. Likewise, the self-metathesis of the asymmetrical butylene isomers, namely butene-1 and isobutylene, is similarly expected to result in the production of both lower and higher carbon number olefins, namely ethylene and isomers of hexene, as illustrated below:

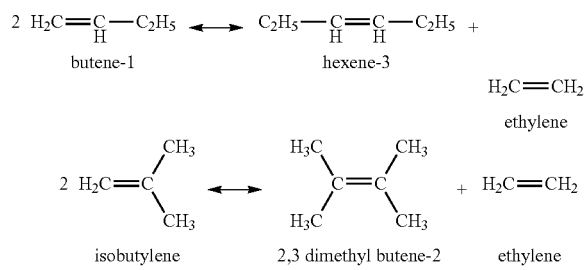

In the metathesis of the symmetrical butylene isomer, butene-2 (where the $R_1$ and $R_2$ groups are the same as $R_3$ and $R_4$, without regard to the cis and trans configuration, i.e., $R_1$=$R_3$=—$CH_3$ and $R_2$=$R_4$=—H or $R_1$=$R_4$=—$CH_3$ and $R_2$=$R_3$=—H), a degenerative result is expected, because the two alkylidene fragments, generated from cleavage of the carbon-carbon double bond, are identical. Thus, the self-metathesis of butene-2 is expected to form butene-2. The formation of these expected olefin metathesis reaction products is experimentally verified in conventional olefin metathesis catalyst and reaction systems.

The tungsten hydride/alumina catalyst described in US 2008/0255328 for olefin metathesis was also previously shown to be effective in alkane metathesis in US 2007/129584. According to this publication, the metathesis of an alkane using the tungsten hydride/alumina catalyst, to produce the next higher and lower carbon number homologues, provides a high selectivity for the normal (unbranched) hydrocarbons.

The art therefore recognizes that (i) the tungsten hydride/alumina catalyst system is effective in paraffin and olefin metathesis, and (ii) the self-metathesis of all $C_4$ olefin isomers (i.e., the isomers of butylene, namely butene-1, butene-2 (both cis and trans configurations), and isobutylene) forms olefins having either 2, 4, or 6 carbon atoms. Surprisingly, however, experimental results now directly contradict expectations based on this knowledge. In particular, it has been discovered that hydrocarbon feedstocks comprising predominantly (e.g., greater than 50% by weight of) butylene (e.g., where the butylene comprises all or a large proportion of a single isomer of butylene) can be contacted with a particular type of catalyst having a known olefin metathesis function, under olefin metathesis conditions, to produce appreciable quantities of propylene (having 3 carbon atoms) in addition to olefins of higher carbon numbers, relative to butylene. The catalyst found to unexpectedly provide this result comprises a solid support and a tungsten hydride bonded to alumina present in the support.

Representative processes according to the invention can therefore advantageously produce propylene from a single carbon number olefin, namely butylene (a 4 carbon number olefin), and in some cases even from a single isomer of butylene, rather than relying on the cross-metathesis of olefins of differing carbon numbers (e.g., in the reaction between ethylene and butylene to produce propylene). This provides a number of commercial advantages over conventional propylene production methods via olefin metathesis, including eliminating the need for sources of different feedstock components at the same location. For example, ethylene is typically obtained as a product of steam cracking, and in particular is recovered as a low boiling fraction from an ethylene/ethane splitter. Butylene, on the other hand, may be obtained from crude oil refining operations or non-petroleum based processes. While sources of both ethylene and butylene may be present at a given location, this is not necessarily the case. Moreover, butylene is generally a less expensive feedstock component than ethylene, meaning that the overall economics of propylene production from butylene may be considerably improved, compared to those of conventional olefin metathesis processes involving reaction between ethylene and butylene.

Accordingly, embodiments of the invention relate to processes for producing propylene, comprising contacting a hydrocarbon feedstock comprising butylene with a catalyst comprising a solid support and a tungsten hydride bonded to alumina present in the support. The feedstock, or at least the olefin portion of the feedstock (portion comprising olefinic hydrocarbons), comprises predominantly butylene (i.e., butene-1, cis-butene-2, trans-butene-2, isobutylene, and/or mixtures thereof), and often butylene is present in an amount of at least 80% by weight of total olefins in the hydrocarbon feedstock. More particular embodiments of the invention relate to processes for producing propylene comprising contacting a hydrocarbon feedstock comprising predominantly butene-1, isobutylene, or a mixture of butene-1 and isobutylene with a catalyst comprising a solid support and a tungsten hydride bonded to alumina present in the support.

According to some embodiments, the hydrocarbon feedstock may be substantially free of isobutylene due to upstream removal of this branched olefin using, for example, a shape-selective molecular sieve, with the remaining butene-1 and butene-2 isomers being present at substantially their equilibrium concentrations on an isobutylene-free basis. Advantageously, propylene can be produced using such feedstocks, having a butene-2 (both cis and trans isomers): butene-1 molar ratio of greater than 3, for example in the range from about 3 to about 10, without further treatment (e.g., to separate butene-2). In further embodiments, therefore, the hydrocarbon feedstock may comprise a mixture of butene-1 and butene-2, present in an amount of at least 50% by weight of the butylene. Often this mixture, having a butene-2: butene-1 molar ratio as indicated above, is present in an amount of at least about 90%, or at least about 95%, by weight of the butylene.

According to embodiments using any mixture of butylene isomers, a per pass conversion of the butylene (i.e., based on the conversion of all $C_4$ olefins) in the hydrocarbon feedstock is at least about 15% (e.g., in the range from about 20% to about 60%) by weight, and the butylene is converted to propylene with a selectivity of at least about 20% (e.g., in the range from about 20% to about 65%) by weight, and often in the range from about 40% to about 60% by weight.

These and other aspects and embodiments associated with the present invention are apparent from the following Detailed Description.

Figure 1:
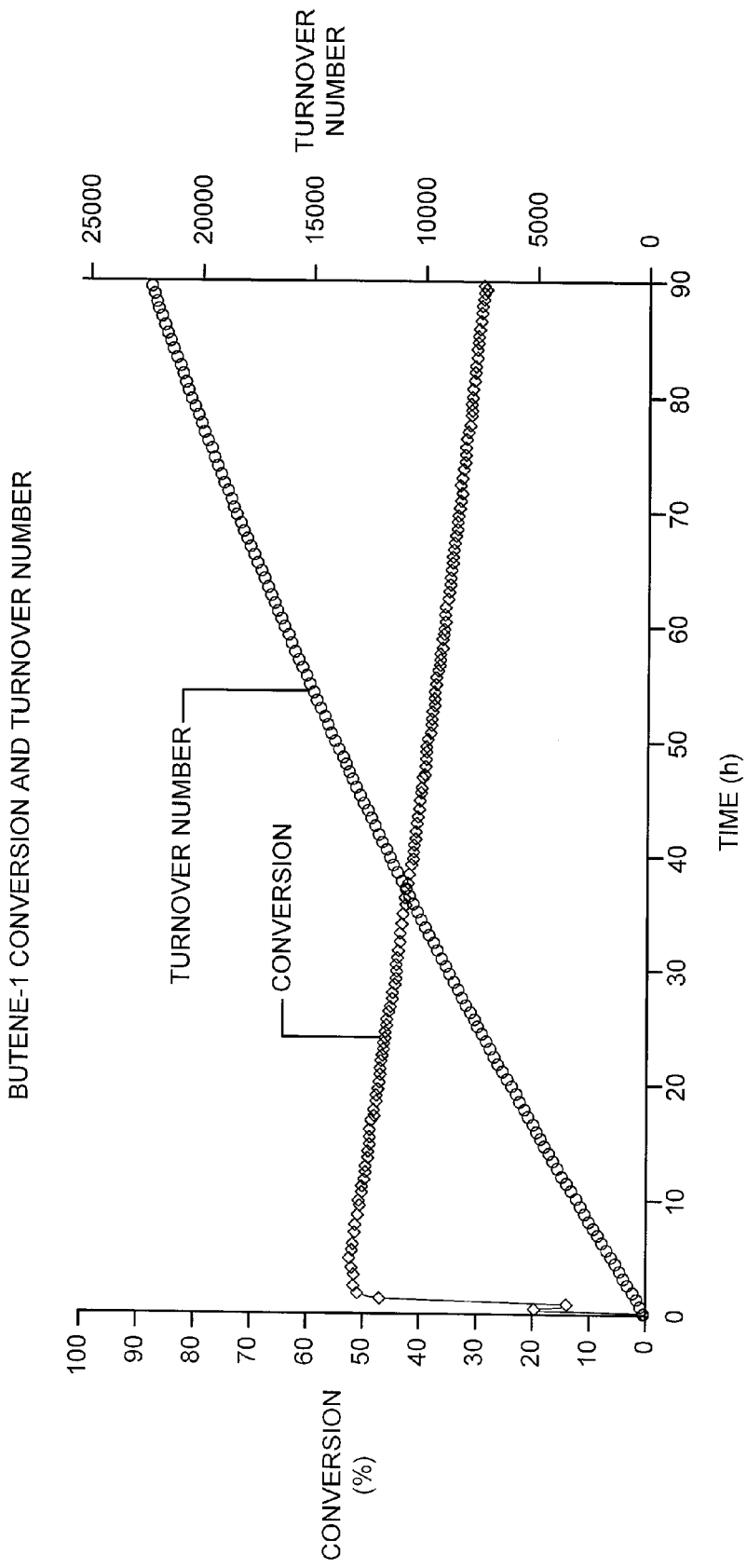
FIG. 1 is a graph showing the (i) conversion of butylene and (ii) turnover number (i.e., total moles of butene-1 converted per mole of tungsten metal in the catalyst) as a function of time on stream. The conversion data were obtained in the production of propylene from butene-1.

The catalyst used to obtain the data presented in FIGS. 1-8 was a catalyst comprising a tungsten hydride bonded to alumina present in the support.

DETAILED DESCRIPTION

As discussed above, the present invention is associated with catalyst systems for olefin metathesis (or disproportionation) processes in which a hydrocarbon feedstock is contacted, in a metathesis reactor or reaction zone. Importantly, it has now been discovered that such catalyst systems, in which a tungsten hydride is bonded to alumina present in the catalyst support, effectively convert hydrocarbon feedstocks comprising predominantly, substantially all, or all butylene ($C_4$ olefins) to propylene with high selectivity. This has been verified in tests in which butylene is present as a single $C_4$ olefin isomer (e.g., butene-1) or as a mixture of $C_4$ olefin isomers (e.g., a mixture of butene-1 and butene-2). As discussed above, the use of catalysts and process conditions for olefin metathesis would not be expected to produce propylene in appreciable quantities. The finding contrary to this expectation, namely that butylene can be converted to propylene in an olefin metathesis environment, has important commercial implications in view of the generally higher value, per unit weight, of propylene relative to butylene (regardless of the relative quantities of $C_4$ olefin isomers).

The hydrocarbon feedstock, comprising butylene as discussed above, refers to the total, combined feed, including any recycle hydrocarbon streams, to a reactor or reaction zone having a catalyst as described herein and under reaction conditions including those that are normally effective for olefin metathesis. The hydrocarbon feedstock does not include any non-hydrocarbon gaseous diluents (e.g., nitrogen), which may be added according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in processes according to the present invention, the hydrocarbons contained in the hydrocarbon feedstock are generally predominantly (i.e., at least 50% by weight, such as from about 60% to about 100% by weight) olefins, and in many cases all or a large proportion (e.g., from about 80% to about 100% or even from about 90% to about 100%) of the olefins are butylene (i.e., $C_4$ olefins including any or all of the structural and positional isomers, namely butene-1, cis-butene-2, trans-butene-2, and isobutylene). For example, butene-1, butene-2, and isobutylene, may in combination represent substantially all of the olefin portion, and predominantly the hydrocarbon portion, of the hydrocarbon feedstock. In more particular embodiments, butylene is present in an amount of at least about 75% (e.g., from about 75% to about 100%) by weight, and often in an amount of at least about 85% (e.g., from about 85% to about 100% or from about 95% to about 100%) by weight, based on the total hydrocarbons of the hydrocarbon feedstock. In other embodiments, the above percentage ranges for butylene are representative of its contribution to the total olefins present in the hydrocarbon feedstock. In still other embodiments, the above percentage ranges for butylene are representative of its contribution to the total hydrocarbon feedstock, rather than its contribution to the total hydrocarbons or the total olefins present in the hydrocarbon feedstock.

In yet further embodiments, the above percentage ranges, namely at least 50% (e.g., from about 60% to about 100%) by weight, at least about 75% (e.g., from about 75% to about 100%) by weight, and at least about 85% (e.g., from about 85% to about 100% or from about 95% to about 100%) by weight, are representative of the percentage of a particular $C_4$ olefin isomer (e.g., butene-1, butene-2 (both cis and trans isomers), or isobutylene) with respect to (i) the total hydrocarbons in the hydrocarbon feedstock, (ii) the total olefins in the hydrocarbon feedstock, (iii) the total hydrocarbon feedstock, or even (iv) the total butylene in the hydrocarbon feedstock. In still further embodiments, the hydrocarbon feedstock may comprise all or a large proportion (e.g., from about 80% to about 100% or even from about 90% to about 100%) of one of the particular butylene isomers (e.g., butene-1, butene-2, or isobutylene). In a representative embodiment, the hydrocarbon feedstock comprises at least about 50% by weight of butene-1, isobutylene, or a mixture of butene-1 and isobutylene.

To achieve a sufficient concentration of any desired isomer, for example butene-1, in the hydrocarbon feedstock, it may be desirable to purify this olefin reactant from the other $C_4$ olefin isomers. In many cases, for example, the $C_4$ olefin isomer of interest is present in refinery or non-petroleum based process streams as a mixture that is at or near equilibrium with these other isomers. It may be advantageous to use such a mixture as the hydrocarbon feedstock (or combine such a mixture, as a hydrocarbon feedstock component, with a recycle stream, as discussed below, to provide the hydrocarbon feedstock), without separation or purification of any desired isomer(s). Otherwise, separation of a desired isomer (e.g., butene-1), upstream of the reactor or reaction zone, to a purity substantially in excess of its equilibrium concentration may be achieved using known techniques including distillation and adsorptive separation (including moving bed and simulated moving bed systems known in the art). In any such separation, generally a stream rich in isomers (e.g., butene-2 and isobutylene) other than the desired isomer (i.e., a stream containing either or both of these other isomers in a concentration in excess of equilibrium) is also produced. Subjecting this stream to isomerization to restore equilibrium or near equilibrium levels of isomers can then generate an additional amount of the desired isomer for contacting with the tungsten hydride/alumina catalyst, as described herein. For example, suitable isomerization catalysts and processes for restoring equilibrium concentrations of $C_4$ olefins in a mixture of butenes having a sub-equilibrium concentration of any particular $C_4$ olefin(s) are known in the art and include, for example, magnesium oxide containing isomerization catalysts as described in U.S. Pat. No. 4,217,244.

Integrated processes according to aspects of the invention therefore include separating, using a separation process (e.g., distillation or adsorptive separation), a desired $C_4$ olefin isomer (e.g., butene-1, butene-2, or isobutylene) from an impure mixture of this $C_4$ olefin isomer with other $C_4$ olefin isomers to provide a stream rich in the desired $C_4$ olefin isomer (i.e., having a concentration of butene-1, butene-2, or isobutylene above its equilibrium concentration with the other olefin isomers) and a stream lean in the desired $C_4$ olefin isomer (i.e., having a concentration of butene-1, butene-2, or isobutylene below its equilibrium concentration with the other olefin isomers). The hydrocarbon feedstock that is contacted with the tungsten hydride/alumina catalyst, according to this embodiment, comprises at least a portion of the stream rich in the desired $C_4$ olefin isomer. Optionally, the stream lean in the desired $C_4$ olefin isomer is then isomerized to provide an isomerization product comprising an additional amount of the desired $C_4$ olefin isomer, and this isomerization product may be recycled to the separation process to which the impure mixture, described above, is also fed.

In other embodiments, it may be desirable to increase the content of the desired $C_4$ olefin (e.g., butene-1) in the hydrocarbon feedstock by subjecting an impure mixture of this olefin with other $C_4$ olefin isomers (e.g., in the case where the impure mixture is lean in the desired $C_4$ olefin isomer, such that it has a concentration below its equilibrium concentration with the other olefin isomers) to isomerization to convert, for example, butene-2 and isobutylene to additional butene-1. The isomerization may be performed in a reactor or reaction zone that is separate from (e.g., immediately upstream of) the reactor or reaction zone containing the tungsten hydride/alumina catalyst. Alternatively, the isomerization may be performed in the same reactor that contains this catalyst, for example by incorporating an isomerization catalyst upstream of the tungsten hydride/alumina catalyst or even by combining the two catalysts in a single catalyst bed.

Further aspects of the present invention are directed to the production of propylene and one or more other olefin products from a hydrocarbon feedstock comprising hydrocarbons that are predominantly butylene, as described above. The other olefin products are generally ethylene, pentene (encompassing all structural and positional isomers of the $C_5$ olefins, including pentene-2, pentene-2,2-methyl butene-1,3-methyl butene-1,2-methyl butene-2,3-methyl butene-2, etc.), hexene (encompassing all structural and positional isomers of the $C_6$ olefins), and/or higher olefins. These olefin products are produced with varying selectivities, referring to the weights of these products produced, divided by the total weight of converted butylene. Advantageously, propylene is often the olefin product having the highest selectivity.

The butylene, which may be purely a single $C_4$ olefin isomer (e.g., butene-1) or otherwise a mixture of isomers, can be derived from petroleum or non-petroleum sources. Crude oil refining operations yielding olefins, and particularly butylene (as a mixture of the $C_4$ olefins butene-1, butene-2, and isobutylene), include hydrocarbon cracking processes carried out in the substantial absence of hydrogen, such as fluid catalytic cracking (FCC) and resid catalytic cracking (RCC). Various olefins including butylene are recovered in enriched concentrations from known separations, including fractionation, of the total reactor effluents from these processes. Non-petroleum sources of butylene include products of oxygenate to olefins conversion processes, and particularly methanol to light olefins conversion processes. Such processes are known in the art, as discussed above, and optionally include additional conversion steps to increase the butylene yield such as by dimerization of ethylene and/or selective saturation of butadiene, as described in U.S. Pat. No. 7,568,018. According to particular embodiments of the invention, therefore, at least a portion of the butylene in the hydrocarbon feedstock is obtained from an oxygenate to olefins conversion process.

In representative olefin production processes, with an exemplary process being the conversion of butene-1, optionally in combination with butene-2 and/or isobutylene, for the production of the higher value product propylene, catalysts comprising a solid support and a tungsten hydride bonded to alumina present in the support (i.e., the tungsten hydride/alumina catalyst), may be used to achieve economically favorable product yields under commercial process conditions, including process conditions known to be effective for olefin metathesis. The per pass conversion level of butylene, based on the conversion of all $C_4$ olefins in the hydrocarbon feedstock, is generally at least about 15% by weight and typically from about 20% to about 60% by weight.

In one or more separations (e.g., fractionation) of the reactor or reaction zone effluent downstream of the reactor or reaction zone where the hydrocarbon feedstock is contacted with the tungsten hydride/alumina catalyst, the desired product (e.g., propylene) may be recovered in substantially pure form by removing and recovering (I) unconverted $C_4$ olefins originally present as butylene in the hydrocarbon feedstock, and (II) other reaction products (e.g., one or more fractions comprising $C_5^+$ hydrocarbons including olefin oligomers and alkylbenzenes). Recycling of all or a portion of (I) back to the reactor or reaction zone may often be desirable for achieving complete or substantially complete overall conversion, or at least significantly higher overall conversion (e.g., from about 80% to about 100% by weight, or from about 95% to about 100% by weight) than the per pass conversion levels of butylene, as indicated above. In other embodiments, it may be desirable to further separate (I) into (Ia) a fraction rich in the desired $C_4$ olefin isomer, relative to (I) and (Ib) a fraction lean in the desired $C_4$ olefin isomer, relative to (I), with streams (Ia) and (Ib) often having concentrations of the desired $C_4$ olefin isomer above and below, respectively, its equilibrium concentration with the other $C_4$ olefin isomers. In this case, all or a portion of (Ia) may be recycled directly back to the reactor or reaction zone, while all or a portion of (Ib) may be isomerized, as described above, to provide an isomerization product comprising an additional amount of the desired $C_4$ olefin isomer, and all or a portion of this isomerization product may be recycled to the reactor or reaction zone or otherwise to a separation process upstream of the reactor or reaction zone, as described above, to separate the desired $C_4$ olefin isomer (e.g., butene-1) in a purified form.

Downstream separation(s) of the olefin product(s) from the reactor or reaction zone effluent, in addition to those described above, are normally carried out to achieve high purity/purities of the desired product(s), particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted butylene (including all $C_4$ olefin isomers) in the hydrocarbon feedstock to the desired olefin product, propylene, is generally at least about 20% (e.g., in the range from about 20% to about 65%) by weight. The selectivity of pentene, which includes all $C_5$ olefin isomers, is generally at least about 15% (e.g., in the range from about 20% to about 60%) by weight, and the selectivity of hexene, which includes all $C_6$ olefin isomers, is generally at least about 2% (e.g., in the range from about 2% to about 45%) by weight. The per pass yield of the desired olefin product and other olefin products is the product of the selectivity to this/these olefin product(s) and the per pass conversion, which may be within the ranges discussed above. The overall yield, using separation and recycle of unconverted $C_4$ olefins, as discussed above, can approach this/these product selectivity/selectivities, as essentially complete conversion is obtained (minus some purge and solution losses of the hydrocarbon feedstock and product(s), as well as losses due to downstream separation inefficiencies).

The conversion and selectivity values discussed above are achieved by contacting the hydrocarbon feedstock described above, either continuously or batchwise, with a tungsten hydride/alumina catalyst as described herein, comprising a solid support and a tungsten hydride bonded to alumina present in the support. Generally, the contacting is performed with the hydrocarbon feedstock being passed continuously through a fixed bed of the catalyst in a reactor or reaction zone, normally under conditions effective for olefin metathesis. For example, a swing bed system may be utilized, in which the flowing hydrocarbon feedstock is periodically re-routed to (i) bypass a bed of catalyst that has become spent or deactivated and (ii) contact a bed of fresh catalyst. A number of other suitable systems for carrying out the hydrocarbon feedstock/catalyst contacting are known in the art, with the optimal choice depending on the particular feedstock, rate of catalyst deactivation, and other factors. Such systems include moving bed systems (e.g., counter-current flow systems, radial flow systems, etc.) and fluidized bed systems, any of which may be integrated with continuous catalyst regeneration, as is known in the art.

As discussed above, the use of the tungsten hydride/alumina catalyst system, in combination with catalyst/feedstock contacting conditions generally favorable for olefin metathesis, surprisingly results in the production of propylene from a hydrocarbon feedstock in which the hydrocarbons are predominantly butylene. Due to the mechanism of the olefin metathesis reaction, which results in redistribution of alkylidene radicals that would be generated upon cleavage of the carbon-carbon double bond of an acyclic olefin, an olefin product having 3 carbon atoms (i.e., propylene) would not be expected in appreciable amounts, regardless of the $C_4$ olefin isomer(s) present in the butylene of the hydrocarbon feedstock. This is especially true in the case of hydrocarbon feedstocks in which the butylene (total $C_4$ olefins) of the hydrocarbon feedstock comprises all or a large proportion (e.g., from about 80% to about 100% or even from about 90% to about 100%) of a single $C_4$ olefin isomer (e.g., butene-1).

Representative conditions for contacting of the hydrocarbon feedstock with the tungsten hydride/alumina catalyst, at which the above conversion and selectivity levels may be obtained, include a temperature from about 75° C. (167° F.) to about 250° C. (482° F.), and often from about 100° C. (212° F.) to about 200° C. (392° F.); an absolute pressure from about 0.1 bar (1.5 psi) to about 100 bar (1450 psi), and often from about 0.5 bar (7.3 psi) to about 35 bar (508 psi); and a weight hourly space velocity (WHSV) from about 1 $hr^{-1}$ to about 100 $hr^{-1}$, and often from about 5 $hr^{-1}$ to about 25 $hr^{-1}$. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally partially or all in the vapor phase in the reactor or reaction zone, but it may also be in the liquid phase, depending on the particular process conditions used.

Importantly, the tungsten hydride/alumina catalysts according to embodiments of the invention and providing the significant benefits, as discussed above, comprise a tungsten hydride that is bonded to alumina present in the support. In general, the support comprises predominantly (i.e., at least 50% by weight) alumina, with the optional addition of other components such as other inorganic refractory metal oxides (e.g., silica, zirconia, titania, boria, thoria, ceria) and/or catalyst promoters or modifiers (e.g., alkali or alkaline earth metals, or transition metals in addition to tungsten). Typically, the support comprises alumina in an amount of at least about 90% (e.g., from about 90% to about 100%) by weight and often at least about 95% (e.g., from about 95% to about 100%) by weight.

The catalyst therefore comprises a support comprising alumina (aluminum oxide) to which a tungsten hydride is covalently bonded (grafted). The term "a tungsten hydride" refers to a tungsten compound that is supported on the catalyst. The tungsten atom of the tungsten compound is bonded to at least one hydrogen atom or hydrocarbon residue by at least one single, double, or triple bond. The tungsten atom is also bonded, through an oxygen linkage, to an aluminum atom of the alumina support. The tungsten hydride may be identified by one or more absorption bands, under infrared (IR) spectroscopy that are characteristic of a (W—H) bond, as described below. Otherwise, the tungsten hydride (W—H) bond may be detected with proton nuclear magnetic resonance (solid $^1$H-NMR) at 500 MHz, where the value of the tungsten hydride chemical shift $\delta_{W-H}$ is typically found at a value of about 10.6 parts per million (ppm) (e.g., in the range from about 10.3-10.9 ppm).

In representative supports, the alumina (aluminum oxide) is accessible to the tungsten hydride at the surface of the support. The support may be a relatively homogeneous composition comprising alumina throughout the mass of the support (e.g., from the core to the surface of the support). Alternatively, the support may be a relatively heterogeneous composition comprising alumina that is present, for example, only at a surface layer. In the latter case, the support may comprise aluminum oxide deposited, supported, or grafted onto an inorganic solid which may itself be an inorganic solid support, for example selected from metals, oxides, sulfides, and salts. Exemplary inorganic solids therefore include other inorganic refractory metal oxides besides alumina.

The support has a surface area generally within a range from 0.1 to 1000 $m^2/g$, and often from about 100 $m^2/g$ to about 450 $m^2/g$. Surface area is measured according to the Brunauer, Emmett and Teller (BET) method based on nitrogen adsorption (ASTM D1993-03 (2008)). The support may comprise all or substantially all aluminum oxide, or it may be mixed with other support components, for example with more than 2% by weight of one or more other inorganic refractory metal oxides (e.g., silica). Also, the aluminum oxide of the support may be modified by one or more elements from groups 14 to 17 of the periodic table of the elements. The elements germanium and tin of group 14 are representative. For element group designations described herein, reference is made to the "CRC Handbook of Chemistry and Physics", $76^{th}$ Edition (1995-1996), by David R. Lide, published by CRC Press, Inc. (USA), in which the groups of the periodic table are numbered 1 to 18.

The alumina of the support may be, for example, a porous alumina, non-porous alumina, a mesoporous alumina, or any mixture of two or all three of these aluminas. Porous aluminas are frequently referred to as "activated aluminas" or alternatively "transition aluminas." Porous aluminas are often partially hydroxylated and obtained by an "activation" treatment comprising heating and dehydration of a precursor selected from aluminum hydroxides (e.g., aluminum tri-hydroxides), hydroxides of aluminum oxide, or gel-form aluminum hydroxides. The activation treatment eliminates water present in the precursor, together with a proportionate amount of the hydroxyl groups, thereby leaving behind some residual hydroxyl groups and a specific porous structure. The surface of porous aluminas generally comprises a complex mixture of aluminum and oxygen atoms, as well as hydroxyl ions, all of which combine according to the specific crystalline form of the alumina and provide both acidic and basic sites. The alumina of the solid support may be a porous alumina selected from Y-alumina (gamma-alumina), η-alumina (eta-alumina), δ-alumina (delta-alumina), θ-alumina (theta alumina), κ-alumina (kappa-alumina), ρ-alumina (rho-alumina) and X-alumina (chi-alumina), and preferably from among Y-alumina, δ-alumina, θ-alumina, and their mixtures. These various crystalline forms depend essentially on the selection of the precursor and the conditions of the activation treatment, in particular temperature and pressure. The activation treatment may be performed, for example, under a stream of air or another gas, such as an inert gas, at a temperature which may be within a range generally from 100° C. (212° F.) to 1000° C. (1832° F.), and typically from 200° C. (392° F.) to 1000° C. (1832° F.).

It is also possible to use porous or alternatively semi-porous aluminas, produced by an activation treatment as previously described, in particular comprising heating to a temperature from 600° C. (1112° F.) to 1000° C. (1832° F.). These porous or semi-porous aluminas may comprise mixtures of porous aluminas in at least one of the previously described crystalline forms, such as Y-alumina, η-alumina, δ-alumina, θ-alumina, κ-alumina, ρ-alumina or X-alumina, with a non-porous alumina (e.g., α-alumina), which may be present in the alumina in widely varying amounts (e.g., from 20% to 80% by weight). Porous aluminas are generally thermal decomposition products of aluminum tri-hydroxides, aluminum oxide hydroxides (or aluminum oxide hydrates), and gel-form aluminum hydroxides (or alumina gels). Aluminum tri-hydroxides of the general formula $Al(OH)_3 = Al_2O_3 \cdot 3H_2O$ may exist in various crystalline forms, such as gibbsite or hydrargillite (α-$Al(OH)_3$), bayerite (β-$Al(OH)_3$), or nordstrandite. Aluminum tri-hydroxides may be obtained by precipitation from aluminum salts in generally alkaline solutions. Aluminum oxide hydroxides of the general formula $AlO(OH) = Al_2O_3 \cdot H_2O$ may also exist in various crystalline forms, such as diaspore β-AlO(OH)) or boehmite (or α-AlO(OH)). Diaspore may be found in certain types of clay and bauxite, and may be synthesized by heat treatment of gibbsite at about 150° C. (302° F.) or by hydrothermal treatment of boehmite at about 380° C. (716° F.) under a pressure of about 500 bar (7250 psi). Boehmite may readily be obtained by heating the resultant gel-form precipitate with cold treatment of the aluminum salt solutions with ammonia. Aluminum oxide hydroxides may also be obtained by hydrolysis of aluminum alcoholates.

Gel-form aluminum hydroxides (or alumina gels) are generally aluminum polyhydroxides, in particular of the general formula: $nAl(OH)_3 \cdot (n-1)H_2O$, in which n is a number ranging from 1 to 8. Gel-form aluminum hydroxides may be obtained by one of the methods selected from among thermal decomposition of an aluminum salt, such as aluminum chloride, electrolysis of an aluminum salt, such as a mixture of aluminum sulfate and an alkali metal sulfate, hydrolysis of an aluminum alcoholate, such as aluminum methylate, precipitation from aluminates, such as an alkali metal or an alkaline-earth metal aluminate, and precipitation from an aluminum salt, for example by contacting an aqueous solution of $Al_2(SO_4)_3$ and ammonia, or of $NaAlO_2$ and an acid, or of $NaAlO_2$ and $Al_2(SO_4)_3$, after which the resultant precipitate may undergo aging and drying to remove water. Gel-form aluminum hydroxides generally assume the form of an amorphous alumina gel, and in particular the form of a pseudoboehmite.

Porous aluminas may have a specific surface area (BET) generally in a range from 50 $m^2/g$ to 1000 $m^2/g$, typically from 75 $m^2/g$ to 600 $m^2/g$, and often from 100 $m^2/g$ to 450 $m^2/g$, with a range from 100 $m^2/g$ to 250 $m^2/g$ being exemplary. They may furthermore have a specific pore volume of generally at most 1 $cm^3/g$, typically at most 0.9 $cm^3/g$, and often at most 0.75 $cm^3/g$.

Non-porous aluminas include α-alumina (alpha-alumina), generally known as "calcined alumina" or "flame alumina" and existing a natural state known as "corundum." They may in general be synthesized by a heat treatment, and in particular calcination, of a precursor selected from aluminum salts, aluminum oxide hydroxides, aluminum tri-hydroxides, and aluminum oxides, such as Y-alumina, at a temperature of greater than 1000° C. (1832° F.), and often greater than 1100° C. (2012° F.). Non-porous aluminas may contain impurities, such as other oxides, for example $Fe_2O_3$, $SiO_2$, $TiO_2$, CaO, $Na_2O$, $K_2O$, MgO, SrO, BaO and $Li_2O$, in proportions of less than 2% by weight, and often less than 1% by weight. They may have a specific surface area (BET) generally in a range from 0.1 $m^2/g$ to less than 300 $m^2/g$, typically from 0.5 $m^2/g$ to 300 $m^2/g$, and often from 0.5 $m^2/g$ to 250 $m^2/g$. The support may also comprise a mesoporous alumina, for example having a surface area (BET) generally in the range of from 100 $m^2/g$ to 800 $m^2/g$. Mesoporous aluminas generally have pores of an average width of from 2 nm to 0.05 μm.

As discussed above, the support may also comprise mixed aluminum oxides, or aluminum oxides combined with at least one other oxide in an amount generally from 2% to less than 80% by weight, typically from 2% to less than 50% by weight, and often from 2% to less than 40% by weight, with an amount from 2% to less than 30% by weight being exemplary. The other oxide(s) may be oxides of an element, M, selected from among metals of groups 1 to 13 and elements of group 14, with the exception of carbon, of the periodic table of the elements. More particularly, they may be oxides of an element M selected from alkali metals, alkaline-earth metals, transition metals and elements of groups 13 and 14, with the exception of carbon. Transition metals generally comprise the metals of groups 3 to 11, and often the elements 21 to 29, 39 to 47, 57 to 79 (including lanthanides) and actinides. The other oxide(s) are often oxides of an element M selected from transition metals of groups 3 to 7, lanthanides, actinides, and elements of groups 13 and 14, with the exception of carbon. More particularly, they may be selected from oxides of silicon, boron, gallium, germanium, titanium, zirconium, cerium, vanadium, niobium, tantalum, chromium, molybdenum, and tungsten.

The support may have a homogeneous composition throughout the entire mass of the support, or it may be heterogeneous and comprise, for example an aluminum oxide, mixed aluminum oxide, or modified aluminum oxide, as previously described, in the form of a surface layer of the support having a thickness that is less than a smallest dimension of the support, for example less than the diameter of a spherical support or less than the diameter of the circular cross section of a cylindrical support. In the case of a heterogeneous composition for the support, the core of the support (e.g., the portion that is not the surface layer) may comprise or consist of an inorganic solid selected from a metal, an oxide, a sulfide, and a salt. Inorganic refractory metal oxides are representative. The heterogeneous support may be prepared by dispersion, by precipitation, and/or by grafting of one of the precursors of aluminum oxide, as described above, onto the inorganic solid. Suitable precursors may include aluminum hydroxides, such as aluminum tri-hydroxides, aluminum oxide hydroxides, and gel-form aluminum hydroxides. Gel-form aluminum hydroxides (known as alumina gels or amorphous aluminas), as described previously, are preferred. A heterogeneous support may for example be produced by processing such a precursor by a sol-gel method or with the assistance of an organometallic compound that facilitates grafting onto the inorganic solid.

The catalyst, comprising a solid support comprising alumina, generally has the form of discreet particles of varying shapes and sizes. For example, the particles may have an average size of generally from 10 nm to 5 mm, and often from 20 µm to 4 mm. The particles may assume their natural shape or may be shaped to have any of a number of forms, including a spherical, a spheroidal, a hemispherical, a hemispheroidal, a cylindrical or a cubic form, or the catalyst may assume the form of a rings, a tablet, a disc, or a pellet.

The catalyst essentially comprises a tungsten hydride that is grafted (covalently bonded) to alumina present in the support, generally by at least one single bond. The oxidation state of the tungsten hydride may have a value in a range from 2 to 6, and often from 4 to 6, which refers to the average oxidation state of tungsten atoms bonded to the alumina support. The tungsten hydride may furthermore be bonded to one or more atoms of hydrogen by single bonds (W—H) and optionally to one or more hydrocarbon residues, R, by single or multiple carbon-tungsten bonds. The number of hydrogen atoms bonded to an atom of tungsten depends on the oxidation state of tungsten, the number of single bonds between the tungsten atom and the support, and optionally the number of single or multiple bonds between the tungsten atom and a hydrocarbon residue, R. Thus, the number of hydrogen atoms bonded to a tungsten atom may be at least equal to 1 and at most equal to 5, and typically ranges from 1 to 4, and often from 1 to 3. Grafting or bonding of the tungsten hydride onto the solid support generally means that the tungsten atom is bonded by at least one single bond to alumina present in the support, and more particularly by at least one single bond (W—OAl) to at least one oxygen atom of the alumina. The number of single bonds between the tungsten atom and the alumina present in the support, in particular by a single bond (W—OAl), depends on the oxidation state of the tungsten and on the number of other bonds of the tungsten atom, and this number is generally 1, 2, or 3.

The tungsten atom of the tungsten hydride may optionally be bonded to one or more hydrocarbon residues, R, with one or more single, double, or triple carbon-tungsten bonds. The hydrocarbon residue(s), R, may be identical or different, saturated or unsaturated hydrocarbon residues, comprising, for example, generally from 1 to 20 and often from 1 to 10 carbon atoms. The hydrocarbon residues may optionally comprise silicon, as in the case of an organosilane residue. The hydrocarbon residues may be selected from (i) alkyl residues, such as linear or branched, aliphatic or alicyclic residues, for example alkyl, alkylidene or alkylidyne residues, having, for example, from 1 to 10 carbon atoms, (ii) aryl residues, having, for example, from 6 to 12 carbon atoms, and (iii) aralkyl, aralkylidene or aralkylidyne residues, for example, having from 7 to 14 carbon atoms.

The tungsten atom of the tungsten hydride, in addition to being bonded to alumina present in the catalyst support, may be bonded to the hydrocarbon residue, R, by one or more single, double, or triple carbon-tungsten bonds. The bond may be a single carbon-tungsten bond. In this case, the hydrocarbon residue, R, may be an alkyl residue, for example linear or branched, or an aryl residue, for example a phenyl residue, or an aralkylene residue, for example a benzyl residue, or a residue of the formula ($C_6H_5$—$CH_2$—$CH_2$—). An alkyl residue is generally taken to mean a monovalent aliphatic residue obtained from the removal of a hydrogen atom from a carbon atom in a molecule of an alkane, an alkene, or an alkyne. In the particular case of the hydrocarbon residue, R, an alkyl residue also includes a monovalent aliphatic residue obtained from the removal of a hydrogen atom from a carbon atom in a molecule of an organosilane. Alkyl residues therefore include, for example, methyl ($CH_3$—), ethyl ($C_2H_5$—), propyl ($C_2H_5$—$CH_2$—), neopentyl (($CH_3$)$_3$C—$CH_2$—), allyl ($CH_2$=CH—$CH_2$—), alkynyl (R—CC≡C—) (e.g., ethynyl (CH≡C—)), and neosilyl (($CH_3$)$_3$Si—$CH_2$—) residues. The alkyl residue may be, for example, of the formula (R'—$CH_2$—) where R' represents a linear or branched alkyl residue.

A double carbon-tungsten bond may also bond the tungsten hydride to the hydrocarbon residue, R. In this case, the hydrocarbon residue, R, may be an alkylidene residue, which may be linear or branched, or an aralkylidene residue. An alkylidene residue is generally a divalent aliphatic residue originating from the removal of two hydrogen atoms from the same carbon atom in the molecule of an alkane, or an alkene, or an alkyne, or even of an organosilane. Alkylidene residues therefore include, for example, methylidene ($CH_2$=), ethylidene ($CH_3CH$=), propylidene ($C_2H_5$—CH=), neopentylidene (($CH_3$)$_3$C—CH=), or allylidene ($CH_2$=CH—CH=) residue. The alkylidene residue may be, for example, of the formula (R'—CH=) where R' represents a linear or branched alkyl residue. An aralkylidene residue is generally taken to mean a divalent aliphatic residue originating from the removal of two hydrogen atoms from the same carbon in an alkyl, alkenyl or alkynyl residue bonded to an aromatic group.

A triple carbon-tungsten bond may also bond the tungsten hydride to the hydrocarbon residue, R. In this case, the hydrocarbon residue, R, may be an alkylidyne residue, which may be linear or branched, or an aralkylidyne residue. An alkylidyne residue is generally a trivalent aliphatic residue originating from the removal of three hydrogen atoms from the same carbon atom in the molecule of alkane, or an alkene, or an alkyne, or even of an organosilane, for example an ethylidyne ($CH_3$—C≡), propylidyne ($C_2H_5$—C≡), neopentylidyne ($(CH_3)_3C$—C≡) or allylidyne ($CH_2$=CH—C≡) residue. The alkylidyne residue may be, for example, of the formula (R'—C≡), where R' represents a linear or branched alkyl residue. An aralkylidyne residue is generally a trivalent aliphatic residue originating from the removal of three atoms of hydrogen from the same carbon of an alkyl, alkenyl, or alkynyl residue bonded to an aromatic group.

Representative hydrocarbon residues, R, are selected from methyl, ethyl, n-propyl, isopropyl, n-butyl, isobutyl, neopentyl, allyl, neopentylidene, allylidene, neopentylidyne, and neosilyl.

The tungsten atom of the tungsten hydride that is grafted (bonded) to alumina present in the catalyst support may be complexed with one or more hydrocarbon ligands, for example aromatic or carbonyl ligands. A particular type of bonding of the tungsten hydride to alumina through a W—OAl linkage may be represented as follows:

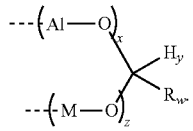

The tungsten hydride bonded to alumina of the support may therefore be represented by the above formula, wherein W, Al, O and H respectively represent atoms of tungsten, aluminum, oxygen and hydrogen, and M represents an atom of one or more elements of another oxide present in the support, as defined previously. R represents a hydrocarbon residue, as defined previously, and w, x, y, and z are integers, the sum of which (w+x+y+z) equals 2 to 6 (i.e., the oxidation state of the tungsten), wherein x=1 to 3, y=1 to 5, w=0 to 4 and z=0 to 2. The value of z is 0, for example, when the tungsten hydride is not bound, through an oxygen linkage, to a metal other than aluminum in the catalyst support. This condition occurs, for example, when the support comprises all or substantially all alumina. In the above formula, the —(Al—O) and -(M-O) bonds represent one or more single or multiple bonds, respectively, bonding the aluminum atom and the metal atom M to one of the atomic constituents of the support comprising alumina, and in particular to one of the oxygen atom constituents of this support.

Under infrared spectroscopy, the catalysts comprising a tungsten hydride, as described herein, generally exhibit one or more absorption bands which are characteristic of the (W—H) bond, the frequency of which bands may vary depending on the coordination sphere of the tungsten and particularly on the number of bonds of the tungsten with the support, with hydrocarbon residues R, and with other hydrogen atoms. Accordingly, at least two absorption bands have been found at 1903 $cm^{-1}$ and 1804 $cm^{-1}$, being characteristic of the (W—H) bond and in particular in the environment of the (W—OAl) bond, bonding the same tungsten atom of the tungsten hydride to an oxygen atom, which is in turn bonded to an aluminum atom of an α-alumina. By way of comparison, tungsten hydride grafted (bonded) under the same conditions onto a silica support generally exhibits under infrared spectroscopy at least one absorption band at 1940 $cm^{-1}$ or 1960 $cm^{-1}$, being characteristic of the (W—H) bond and in particular in the environment of the (W—OSi) bond, bonding the same tungsten atom of the tungsten hydride to an oxygen atom, which is in turn bonded to a silicon atom of the silica support.

The presence of a (W—H) bond of a tungsten hydride, which is bonded to alumina in the catalyst support, may also be detected using proton nuclear magnetic resonance (solid 1H-NMR) at 500 MHz, where the value of the tungsten hydride chemical shift $\delta_{W—H}$ is typically found at a value of about 10.6 parts per million (ppm) (e.g., in the range from about 10.3-10.9 ppm).

In addition to a tungsten hydride, the catalyst may further comprise an aluminum hydride, for example at the surface of the support and/or in the vicinity of the grafted tungsten hydride. Without being bound by theory, it is believed that an aluminum hydride can be formed by opening of an aluminoxane bridge (of the formula Al—O—Al), which may be present at the surface of the support, and by reaction of the opened aluminoxane bridge and a hydrogen atom of a grafted tungsten hydride. A simple method for detecting the presence of aluminum hydride, in addition to tungsten hydride, in the catalyst involves performing a deuteration reaction of the catalyst. According to a particular method, the catalyst is subjected to a deuterium atmosphere under an absolute pressure of 66.7 kPa (10 psi) and a temperature generally from 25° C. (77° F.) to 80° C. (176° F.), and often about 60° C. (140° F.), for a period of about 15 minutes. Selective deuteration under these conditions replaces hydrogen atoms of the (W—H) bond with deuterium atoms, thereby forming (W-D) bonds which, under IR spectroscopy, have absorption bands at 1293 $cm^{-1}$ and 1393 $cm^{-1}$. Selective deuteration leaves the hydrogen atoms in the (Al—H) bonds unchanged, and these bonds may be identified under IR spectroscopy by an absorption band at 1914 $cm^{-1}$.

The solid supported catalyst, comprising a tungsten hydride grafted (bonded) to alumina present in the support, may be prepared by a method comprising dispersion and grafting of an organometallic tungsten precursor (Pr) onto a support comprising alumina. The tungsten in the precursor may be either bonded or otherwise complexed to at least one hydrocarbon ligand, so as to form a hydrocarbon compound or hydrocarbon complex, respectively, of tungsten grafted onto the support. Then, hydrogenolysis of the grafted hydrocarbon compound or hydrocarbon complex of tungsten, resulting from the previous dispersion and grafting, forms tungsten hydride grafted onto alumina of the support.

The organometallic tungsten precursor, Pr, may comprise a tungsten atom bonded to one or more hydrocarbon ligands. The tungsten atom may be bonded to a carbon of the hydrocarbon ligand by single, double or triple (carbon-tungsten) bonds. The hydrocarbon ligands may be identical or different, saturated or unsaturated hydrocarbon residues, for example aliphatic or alicyclic residues, generally having from 1 to 20 carbon atoms and often from about 1 to 10 carbon atoms. The hydrocarbon ligands may be selected from the hydrocarbon residues, R, described previously. The number of hydrocarbon ligands bonded to the tungsten atom depends on the oxidation state of tungsten in the precursor Pr and may be at most equal to this oxidation state. The number of hydrocarbon ligands may therefore be from 1 to 6, typically from 2 to 6, and often from 4 to 6.

The precursor, Pr, may also comprise a tungsten atom complexed to one or more hydrocarbon ligands, the oxidation state of the tungsten being in this case equal to zero. The hydrocarbon ligand may be selected from among aromatic ligands or carbonyl ligands. The precursor Pr may accordingly be selected from among bis-arene tungsten and hexacarbonyl tungsten.

Prior to dispersion and grafting of the organometallic precursor, the support comprising alumina may be subjected to calcination and/or dehydroxylation. Calcination of the support may be performed to oxidize any carbon optionally present in the support and thereby eliminate it as carbon dioxide. Calcination may involve subjecting the support to an oxidizing heat treatment, for example under a stream of dry air, at a temperature below the sintering temperature of the support. Suitable temperatures are generally from 100° C. (212° F.) to 1000° C. (1832° F.), and typically from 200° C. (392° F.) to 800° C. (1472° F.), for a duration sufficient to eliminate the carbon dioxide. The duration may range from 0.1 to 48 hours, and the calcination may be conducted at atmospheric pressure or otherwise under elevated pressure or subatmospheric pressure.

The support may also be subjected to dehydroxylation prior to dispersion and grafting of the organometallic precursor, Pr. Dehydroxylation may be performed to optionally eliminate residual water from the support, as well as a proportion of the hydroxyl groups. A residual quantity of hydroxyl groups is left behind, generally at the surface of the support, and optionally aluminoxane bridges (of the formula Al—O—Al) are formed. Dehydroxylation may be performed by subjecting the support to heat treatment under a stream of inert gas, for example under a stream of nitrogen, argon or helium, under a pressure which is preferably below atmospheric pressure, for example under an absolute pressure of from $10^{-4}$ Pa ($1.5 \times 10^{-8}$ psia) to $10^2$ kPa (14.5 psia), preferably from $10^{-2}$ Pa ($1.5 \times 10^{-6}$ psia) to 50 kPa (7.3 psia), at a temperature below the sintering temperature of the support, for example at a temperature generally from 100° C. (212° F.) to 1000° C. (1832° F.), and typically from 200° C. (392° F.) to 800° C. (1472° F.), and for a duration sufficient to leave behind an appropriate residual quantity of hydroxyl groups and/or aluminoxane bridges in the support. The duration may range from 0.1 to 48 hours. Also, the dehydroxylation step may advantageously be performed after the calcination step.

The dispersion and grafting or bonding of the organometallic precursor, Pr, may be performed by sublimation, by impregnation with the assistance of a solvent, or by dry mixing. In the case of sublimation, the precursor, Pr, which is generally in the solid state under normal conditions, is heated normally under subatmospheric pressure and at a temperature causing its sublimation and migration in the gaseous state onto the support. Sublimation may be performed at a temperature of from −30° C. (−22° F.) to 200° C. (392° F.), and at an absolute pressure from $10^{-4}$ Pa ($1.5 \times 10^{-8}$ psia) to 10 kPa (1.45 psia). Grafting of the precursor, Pr, onto the support may be monitored by IR spectroscopy. Any excess precursor Pr which has not grafted (bonded) onto the support may be removed by inverse sublimation.

The dispersion and grafting may also be performed by impregnation with the assistance of a solvent. In this case, the precursor, Pr, may be dissolved in a polar or non-polar organic solvent, for example pentane or ethyl ether. Impregnation may be performed by contacting the support comprising alumina with the impregnation solution of the precursor, Pr. Impregnation may be performed at a temperature of from −80° C. (−122° F.) to 200° C. (392° F.), under an inert atmosphere, for example an atmosphere of nitrogen, argon and/or helium, and preferably with stirring. In this manner, a suspension of a hydrocarbon compound or a complex of tungsten grafted onto the support is obtained. Any excess precursor Pr which has not grafted (bonded) onto the support may be removed by washing with an organic solvent, which may be identical to or different from that used during impregnation.

The dispersion and grafting may also be performed by dry mixing, including mechanical dry mixing in the absence of liquid or liquid solvent. In this case, the precursor, Pr, which is generally in the solid state under normal conditions, is mixed with the support comprising alumina in the absence of liquid or liquid solvent. Mechanical stirring under an inert atmosphere, for example an atmosphere of nitrogen, argon and/or helium, is used to form a mixture of two solids. During or after the dry mixing, heat and/or subatmospheric pressure may be used to cause migration of the precursor, Pr, and its reaction with and covalent bonding to the support. Any precursor that has not been grafted (bonded) onto the support may be removed by inverse sublimation or washing with organic solvent.

Production of the catalyst may further comprise hydrogenolysis, or reaction of the hydrocarbon compound, or alternatively the hydrocarbon complex, of tungsten grafted onto the support, as prepared in the manner described previously. The reaction is carried out to form a tungsten hydride grafted (bonded) onto the support. Hydrogenolysis is generally understood to mean a reaction involving cleavage of a molecule that accompanies bonding of hydrogen onto the two cleaved ends. Cleavage in this case occurs between the tungsten atom grafted onto the support and the carbon atom of a hydrocarbon ligand that is bonded to or otherwise complexed with the tungsten atom. Hydrogenolysis may be performed with the assistance of hydrogen or a reducing agent that is capable of converting the grafted hydrocarbon compound or hydrocarbon complex of tungsten into grafted tungsten hydride. Hydrogenolysis may be performed by contacting the grafted hydrocarbon compound or hydrocarbon complex of tungsten with the hydrogen or reducing agent. It may be performed under an atmosphere of hydrogen or an inert atmosphere when a reducing agent is used, using an absolute pressure of from $10^{-2}$ Pa ($1.5 \times 10^{-6}$ psia) to 10 MPa (145 psia), at a temperature of from 20° C. (68° F.) to 500° C. (932° F.) for a period of from 0.1 to 48 hours.

Overall aspects of the invention are directed to processes that exploit the unexpected findings found to be associated with the use of a particular catalyst system, known to be effective in olefin metathesis, for the conversion of hydrocarbon feedstocks comprising butylene, which often comprises all or a large proportion of a single $C_4$ olefin isomer (e.g., butene-1). More specifically, operating under process conditions expected to promote olefin metathesis, in the presence of a catalyst comprising a tungsten hydride bonded to alumina present in the catalyst support, provides important commercial advantages in terms of conversion of butylene with good selectivity to propylene. Those having skill in the art, with the knowledge gained from the present disclosure, will recognize that various changes can be made in the above catalysts and processes using the catalysts, without departing from the scope of the present disclosure.

The following examples are representative of the present invention and its associated advantages and are not to be construed as limiting the scope of the invention as set forth in the appended claims.

EXAMPLE 1

Conversion of Butene-1 to Propylene and Other Olefin Products with W—H/Al$_2$O$_3$ Catalysts A solid catalyst comprising a tungsten hydride grafted (bonded) to alumina was prepared as described in Example 3 of US 2007/0129584. The alumina used in this case was Aeroxide® Alu C (Evonik Degussa GmbH, Essen, Germany), having a surface area of 125 m$^2$/g. The tungsten content of the catalyst was 3.0 wt-%, based on the total catalyst weight. The catalyst was evaluated, according to a microreactor-scale experimental protocol, for the production of propylene and other products from a pure butene-1 feedstock under conditions generally favorable for olefin metathesis. In particular, butene-1 was passed over a 150 mg sample loading of the catalyst at a temperature of 150° C. (302° F.) and a flow rate of about 6.6 Nml/min, corresponding to a weight hourly space velocity (WHSV) of about 6.1 hr$^{-1}$. These conditions and 1 barg (15 psig) were maintained over a testing duration of about 90 hours.

Figure 2:
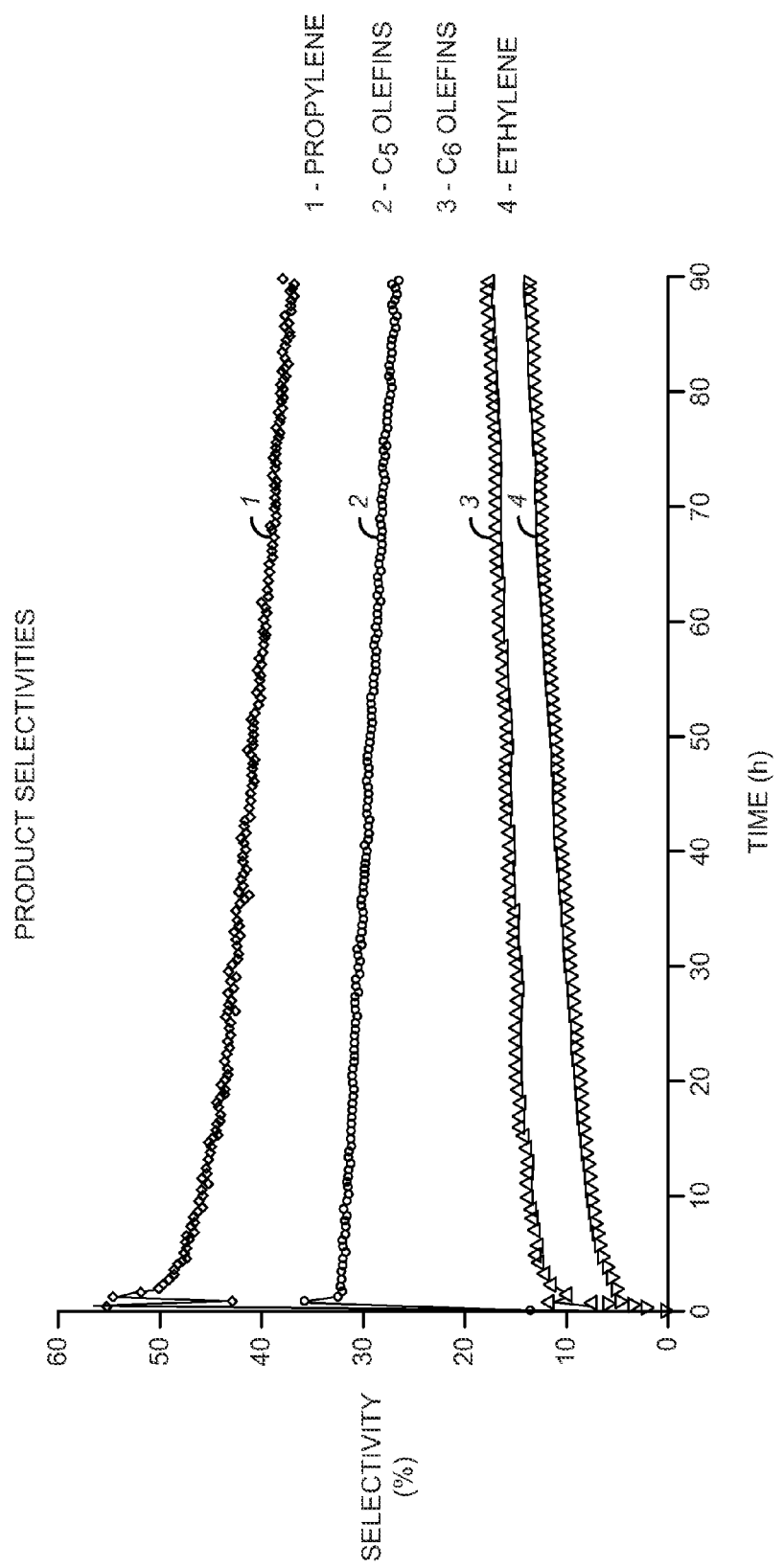
FIG. 2 is a graph showing the selectivities of the main products, propylene and pentene (all $C_5$ olefins), as well as the ethylene and hexene (all $C_6$ olefins), as a function of time on stream. The selectivity data were obtained in the same experiment used to obtain the conversion and turnover number data shown in FIG. 1.

The reactor effluent composition was analyzed periodically by gas chromatography to determine both (i) the conversion level (per pass) of butene-1 and (ii) the turnover number, defined as the total moles of butene-1 converted per mole of tungsten metal in the catalyst, as a function of time on stream. As shown in FIG. 1, a butylene conversion (or butene-1 conversion in this case, since this C$_4$ olefin isomer was the entire hydrocarbon feedstock) reached 53% after about 1 hour on stream, corresponding to the time at which the reactor temperature reached its set point of 150° C. (302° F.). After 90 hours on stream, corresponding to a turnover number of about 22,700, the conversion was about 30%. As shown in FIG. 2, the selectivity to the main product propylene at this time on stream was about 43% by weight. The selectivities to pentene, hexene, and ethylene were about 30%, 16%, and 11%, respectively.

EXAMPLE 2

Effect of Pressure on Conversion of Butene-1 to Propylene and Other Olefin Products The microreactor-scale experimental protocol, for the production of propylene and other products from a pure butene-1 feedstock as described above in Example 1, was repeated except that the catalyst loading was 135 mg, rather than 150 mg, and the flow rate of butene-1 to the reactor containing this loading was 20 Nml/min, rather than 6.6 Nml/min. The weight hourly space velocity therefore increased from about 6.1 hr$^{-1}$ in Example 1 to about 20 hr$^{-1}$ in this example. Also, two separate experiments were performed, maintaining all conditions constant except for pressure, which was 1 barg (15 psig) in one experiment and 20 barg (290 psig) in another.

Figure 3:
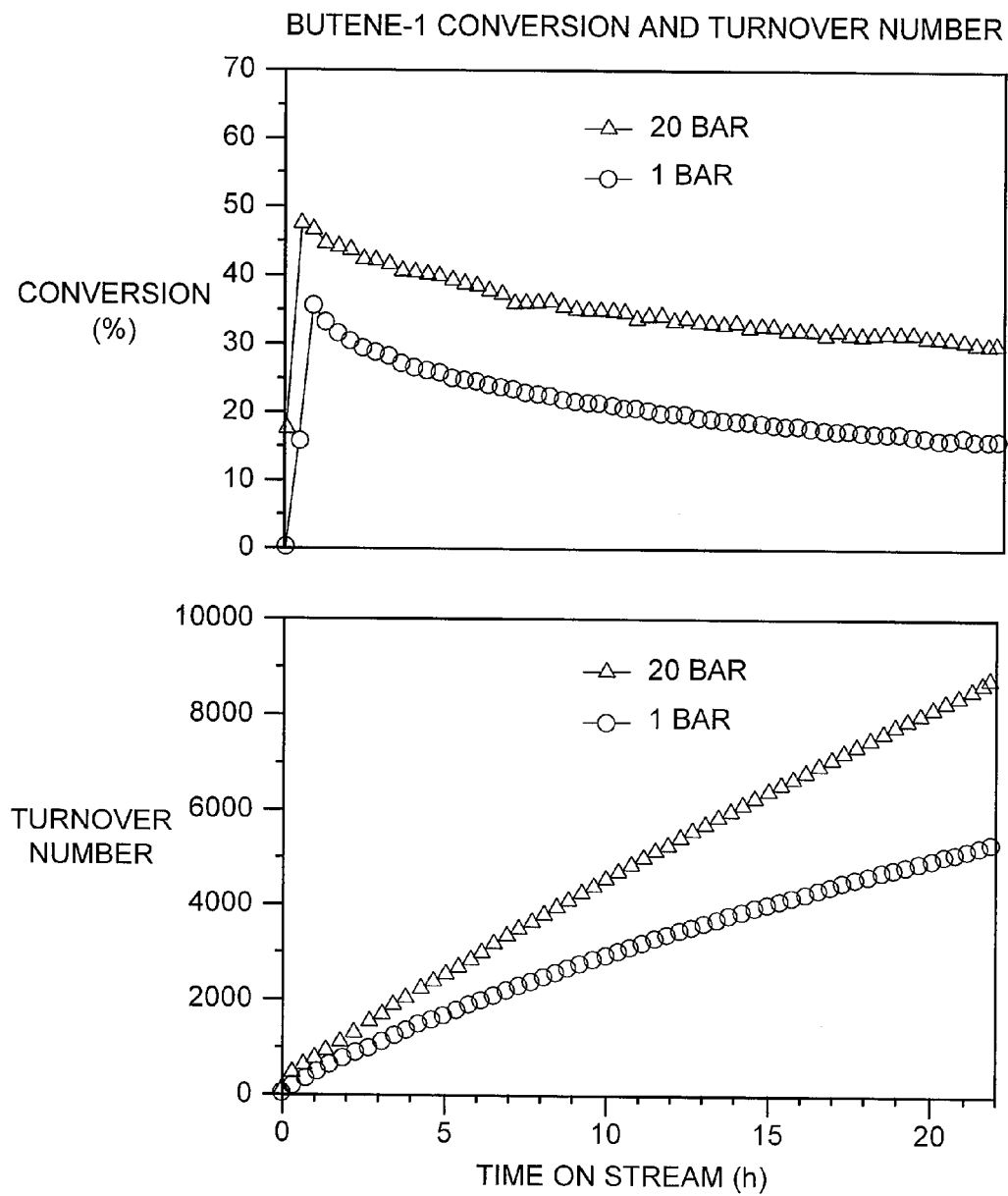
FIG. 3 is a graph showing the (i) conversion of butylene and (ii) turnover number as a function of time on stream, at differing reaction pressures, namely 1 barg (15 psig) and 20 barg (290 psig). The conversion data were obtained in the production of propylene from butene-1.
Figure 4:
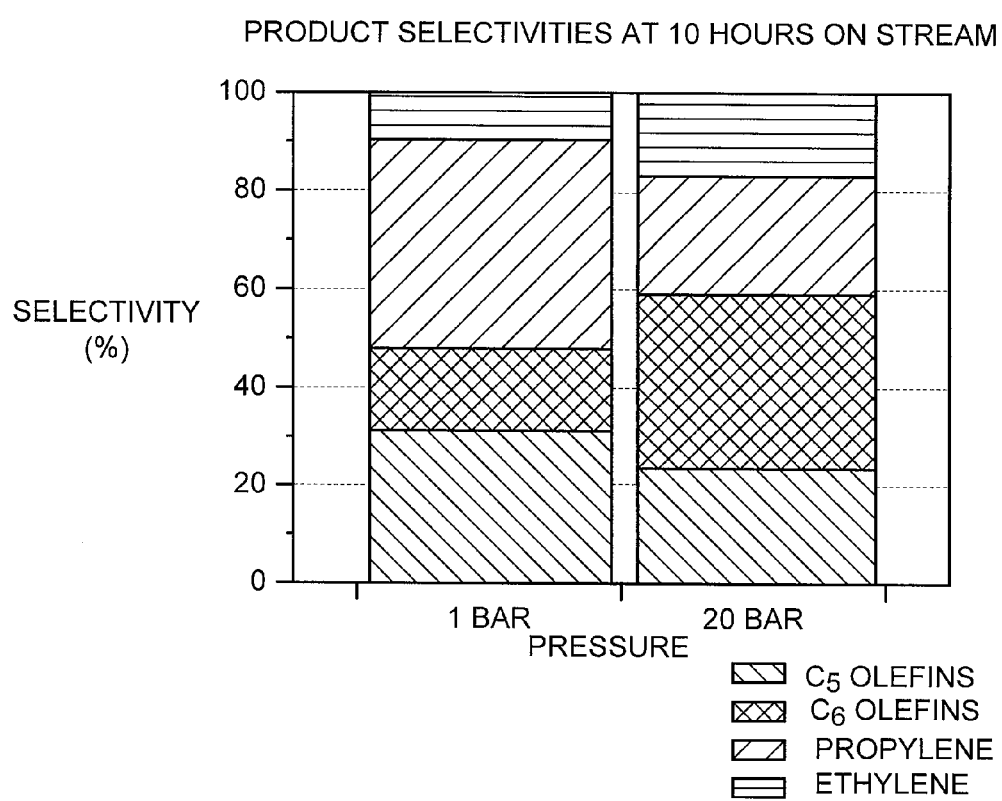
FIG. 4 depicts the selectivities of the main products, propylene and pentene (all $C_5$ olefins), as well as the ethylene and hexene (all $C_6$ olefins), at 10 hours on stream (i.e., 10 hours after initially contacting the catalyst with the hydrocarbon feedstock). The selectivity data were obtained in the same experiments used to test performance (conversion and turnover number) at the different reactor pressures, as described with respect to FIG. 3.

As shown in FIG. 3, the increase in pressure increased the initial conversion of butene-1 from about 35% to about 48%. At 22 hours on stream, the turnover number was about 9000 at the higher pressure, compared to only about 5500 at the lower pressure. Nevertheless, as shown in FIG. 4, the selectivity to the propylene dropped significantly at the higher pressure, from 42% by weight at 1 barg (15 psig) down to only 24% by weight at 20 barg (290 psig). This loss in propylene selectivity at the higher pressure was accompanied by an significant increase in hexene selectivity, from about 17% by weight to about 35% by weight. Therefore, the beneficial effect of increasing pressure on butene-1 conversion was detrimental in terms of propylene selectivity. Without being bound by theory, it is thought that the observed changes in the product slate as a function of pressure were due to the easier absorption of heavier olefins on the catalyst surface, leading to the formation of hexene and higher carbon number products.

EXAMPLE 3

Conversion of an Isobutylene/Butene-2 Mixture to Propylene and Other Olefin Products The microreactor-scale experimental protocol for the production of propylene and other products as described above in Example 1, was repeated except that the feedstock was blend of Isobutylene/Butene-2 (50%/50% on either a molar or weight basis), rather than pure butene-1. Also, the catalyst loading was 400 mg, rather than 150 mg, and the flow rate of butene-1 to the reactor containing this loading was 10 Nml/min, rather than 6.6 Nml/min The weight hourly space velocity therefore decreased from about 6.1 hr$^{-1}$ in Example 1 to about 3.4 hr$^{-1}$ in this example.

Figure 5:
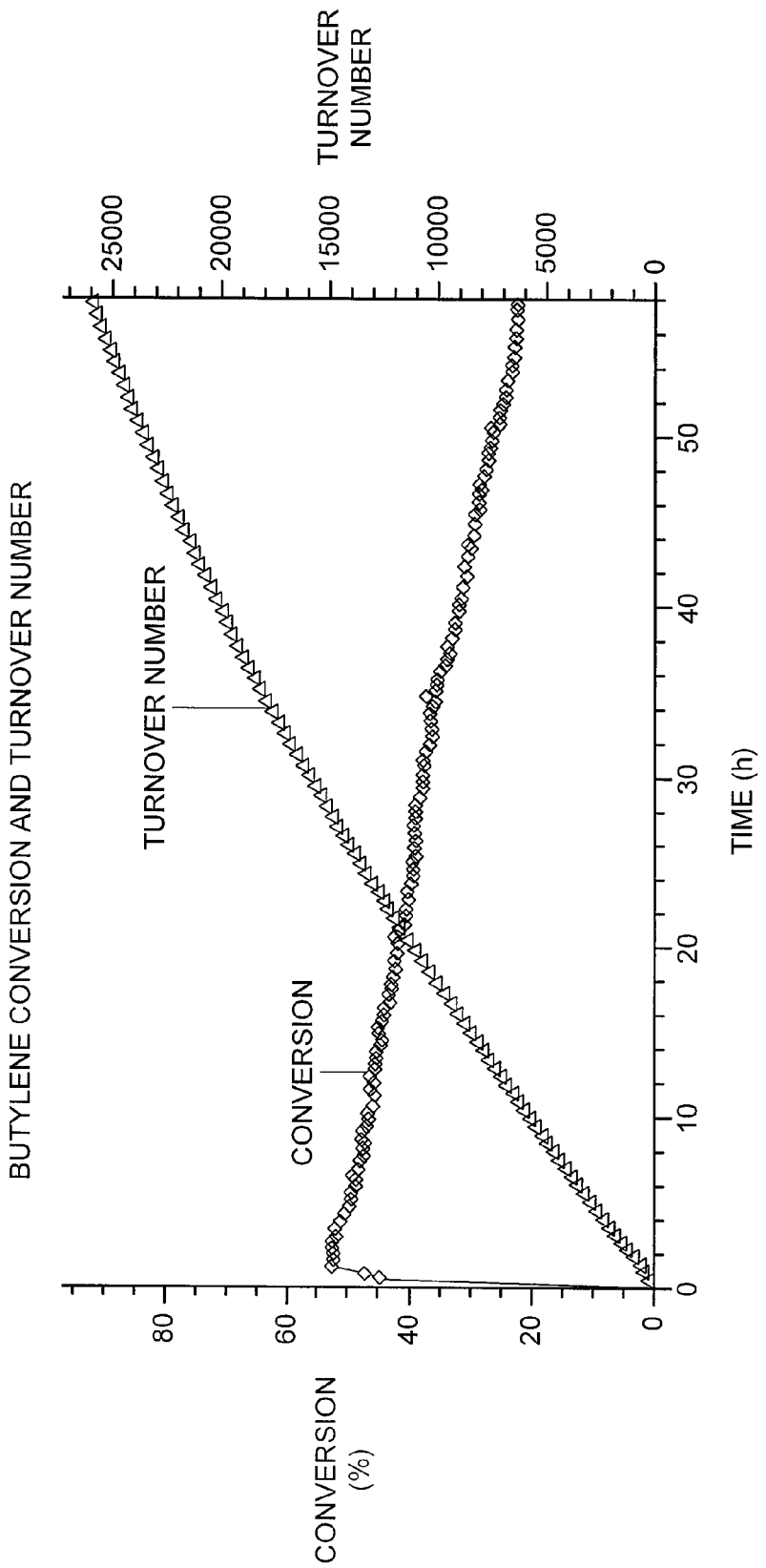
FIG. 5 is a graph showing the (i) conversion of butylene and (ii) turnover number (i.e., total moles of isobutylene and butene-2 converted per mole of tungsten metal in the catalyst) as a function of time on stream. The conversion data were obtained in the production of propylene from an equimolar mixture of isobutylene and butene-2.
Figure 6:
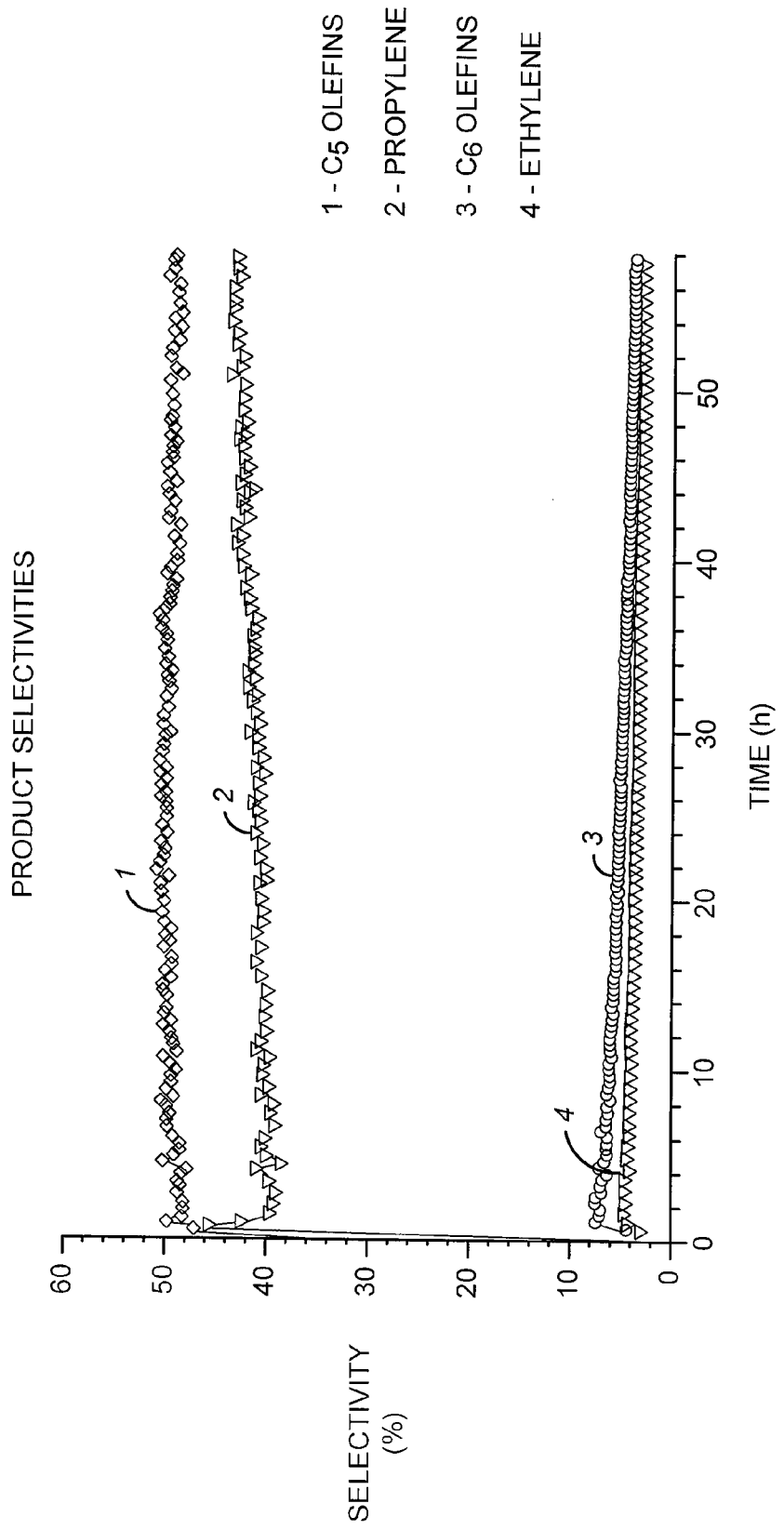
FIG. 6 is a graph showing the selectivities of the main products, propylene and pentene (all $C_5$ olefins), as well as the ethylene and hexene (all $C_6$ olefins), as a function of time on stream. The selectivity data were obtained in the same experiment, with an equimolar mixture of isobutylene and butene-2 as a feed, used to obtain the conversion and turnover number data shown in FIG. 5.

As shown in FIG. 5, a butylene conversion reached 53% initially. After about 60 hours on stream, corresponding to a turnover number of about 26,000, the conversion was about 25%. As shown in FIG. 6, the selectivity to the desired product propylene was steady throughout the run at about 40% by weight. The selectivities to pentene, hexene, and ethylene were about 50%, 5%, and 4%, respectively.

EXAMPLE 4

Conversion of Butene-1/Butene-2 Mixtures to Propylene and Other Olefin Products The microreactor-scale experimental protocol for the production of propylene and other products as described above in Example 2 was repeated with a feedstock of 100% butene-1. Additionally, feedstock blends of butene-1/butene-2 in amounts of 67%/33%, 50%/50%, 33%/67%, and 0%/100% were also tested, while maintaining the same total feedstock flow rate of 20 Nml/min in each case.

Figure 7:
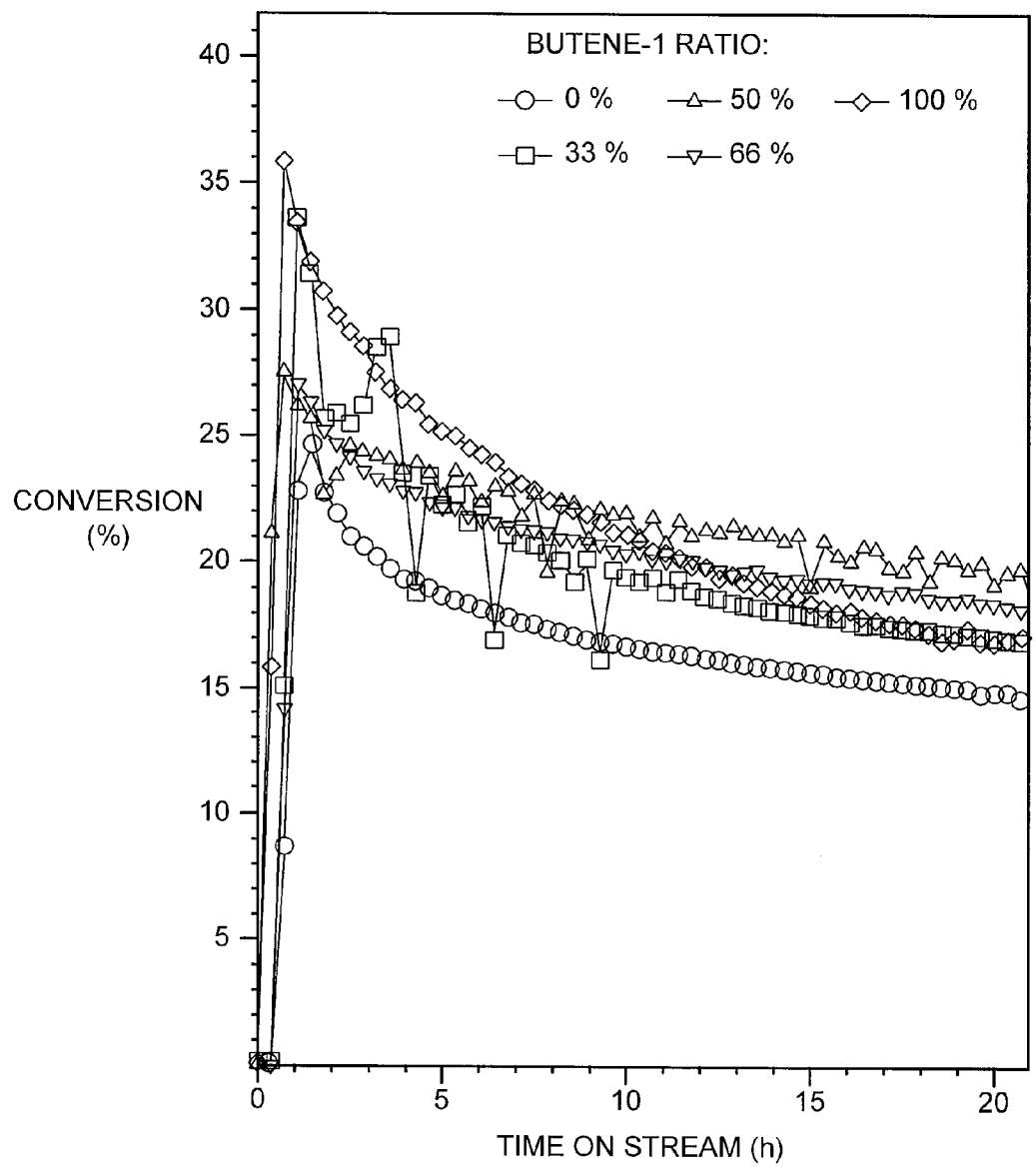
FIG. 7 is a graph showing the conversion of butylene as a function of time on stream, at several different ratios of butene-1/butene-2 in the hydrocarbon feedstock. The conversion data were obtained in the production of propylene from feedstocks with butene-1/butene-2 in amounts of 100%/0%, 67%/33%, 50%/50%, 33%/67%, and 0%/100% being tested.
Figure 8:
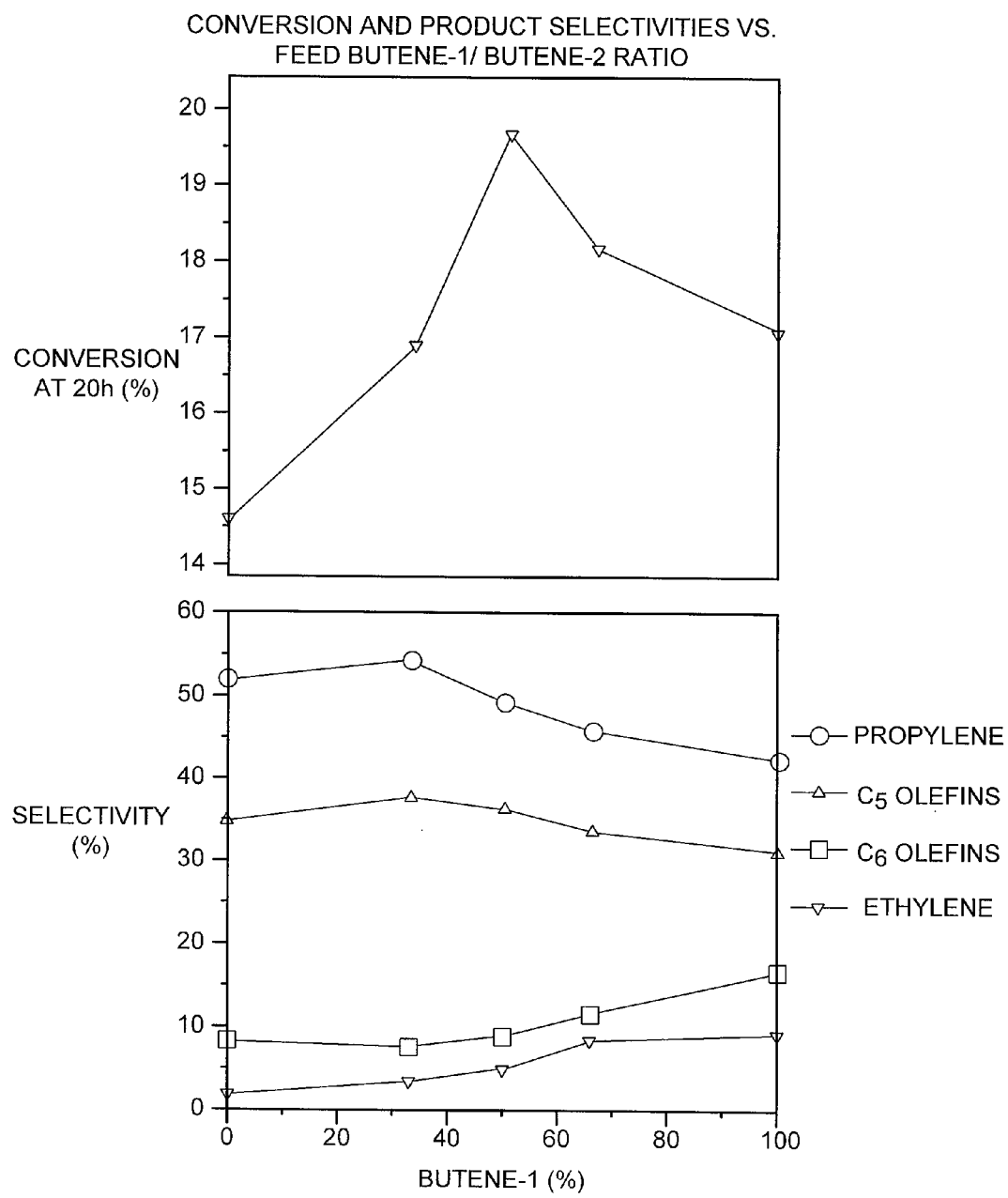
FIG. 8 is a graph showing selectivities of the main products, propylene and pentene (all $C_5$ olefins), as well as the ethylene and hexene (all $C_6$ olefins), as a function of butene-1 content in the butene-1/butene-2 hydrocarbon feedstock. The selectivity data were obtained in the same experiments, used to test performance (conversion) at the different butene-1/butene-2 feed ratios, as described with respect to FIG. 7.

As shown in FIG. 7, the butylene conversion profiles for each blend ratio were similar, with the maximum initial conversion obtained with the feedstock comprising pure butene-1. However, this feedstock also led to the fastest deactivation rate, or decline in butylene conversion over time, such that the 50%/50% butene-1/butene-2 blend provided the highest butylene conversion at 20 hours on stream. This result is also shown in FIG. 8, together with the data showing that a propylene selectivity of 53% by weight was achieved with the 33%/67% butene-1/butene-2 blend.

The data illustrate that butylene, whether present as a single C$_4$ olefin isomer or a mixture of isomers, is effectively converted to higher value propylene and other products, including a significant amount of pentene, under conditions and in the presence of a catalyst that are expected to lead primarily to other products.

The invention claimed is:

1. A process for producing propylene, the process comprising:

contacting a hydrocarbon feedstock consisting of butylene with a catalyst comprising a solid support and a tungsten hydride bonded to alumina present in the support wherein the butylene is converted to propylene with a selectivity of at least 40% by weight.

2. The process of claim 1, wherein the catalyst comprises tungsten in an amount from about 1% to about 10% by weight.

3. The process of claim 1, wherein the support comprises alumina in an amount of at least about 95% by weight.

4. The process of claim 1, wherein the support has a BET surface area from about 100 m$^2$/g to about 450 m$^2$/g, wherein the BET surface area measurement is based on nitrogen adsorption.

5. The process of claim 1, wherein the average oxidation state of tungsten in the tungsten hydride is from 4 to 6.

6. The process of claim 1, wherein the butylene comprises at least 50% by weight of butene-1, butene-2, or a mixture of butene-1 and butene-2.

7. The process of claim 1, wherein the butylene is converted at a per pass conversion of at least about 15% by weight.

8. The process of claim 7, wherein the butylene is converted at a per pass conversion from about 20% to about 60% by weight.

9. The process of claim 1, wherein the butylene is converted to propylene with a selectivity of at least about 53% by weight.

10. The process of claim 1, wherein the butylene is converted to propylene with a selectivity of at least 40% to about 65% by weight.

11. The process of claim 1, wherein the hydrocarbon feedstock is contacted with the catalyst at a temperature from about 75° C. (167° F.) to about 250° C. (482° F.), an absolute pressure from about 0.5 bar (7.3 psi) to about 35 bar (508 psi), and a weight hourly space velocity from about 1 hr$^{-1}$ to about 100 hr$^{-1}$.

12. The process of claim 1, further comprising recovering the propylene with a purity of at least about 99.5% by volume.

13. The process of claim 1, wherein at least a portion of the butylene is obtained from an oxygenate to olefins conversion process or a fluid catalytic cracking process.

14. The process of claim 1, wherein the contacting occurs in a reactor or reaction zone, and the process further comprises separating, from an effluent of the reactor or reaction zone, unconverted butylene.

15. The process of claim 14, further comprising recycling at least a portion of the unconverted butylene back to the reactor or reaction zone.

16. The process of claim 14, further comprising separating the unconverted butylene into a butene-1 rich fraction and a butene-1 lean fraction and recycling at least a portion of the butene-1 rich fraction back to the reactor or reaction zone.

17. The process of claim 16, further comprising isomerizing at least a portion of the butene-1 lean fraction to provide an isomerization product comprising an additional amount of butene-1 and conducting at least a portion of the isomerization product to the reactor or reaction zone, optionally following a separation of at least the portion of the isomerization product to separate butene-1.

18. A process for producing propylene, the process comprising contacting a hydrocarbon feedstock consisting of butene-1, isobutylene, or a mixture of butene-1 and isobutylene with a catalyst comprising a solid support and a tungsten hydride bonded to alumina present in the support, wherein a per pass conversion of $C_4$ olefins in the hydrocarbon feedstock is from about 15% to about 60% by weight and wherein the $C_4$ olefins are converted to propylene with a selectivity of at least 40% by weight.

19. The process of claim 1, wherein the butylene consists of a single isomer of butylene.

20. The process of claim 18 wherein the butylenes consist of 1-butene.

* * * * *